US007094820B2

United States Patent
Zhao et al.

(10) Patent No.: US 7,094,820 B2
(45) Date of Patent: *Aug. 22, 2006

(54) POLYMER ADDITIVE COMPOSITIONS COMPRISING HIGHLY VERSATILE THERMOPLASTIC NUCLEATORS

(75) Inventors: Xiaodong Edward Zhao, Moore, SC (US); Darin L. Dotson, Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 428 days.

This patent is subject to a terminal disclaimer.

(21) Appl. No.: 10/288,040

(22) Filed: Nov. 5, 2002

(65) Prior Publication Data

US 2003/0096895 A1 May 22, 2003

Related U.S. Application Data

(63) Continuation of application No. 09/864,460, filed on May 23, 2001, now Pat. No. 6,559,211.

(51) Int. Cl.
    *C08K 5/09* (2006.01)
(52) U.S. Cl. ..................... 524/285; 252/189
(58) Field of Classification Search ............. 524/285; 252/189
    See application file for complete search history.

(56) References Cited

U.S. PATENT DOCUMENTS

| 3,201,363 | A | 8/1965 | Spurlin et al. ............. 260/30.4 |
| 3,207,736 | A | 9/1965 | Wijga et al. ............... 260/93.7 |
| 3,234,233 | A | 2/1966 | Bolger et al. ............... 260/326 |
| 3,320,267 | A | 5/1967 | Poos et al. .................. 260/295 |
| 3,367,926 | A | 2/1968 | Voeks et al. ............... 260/93.5 |
| 3,527,736 | A | 9/1970 | Averink et al. ............. 260/78.4 |
| 3,793,401 | A | 2/1974 | Nield et al. ................. 260/876 |
| 3,829,450 | A | 8/1974 | Schmerling et al. ..... 260/346.3 |
| 3,873,643 | A | 3/1975 | Wu et al. .................... 260/878 |
| 3,882,194 | A | 5/1975 | Krebaum et al. ........... 260/878 |
| 3,928,687 | A | 12/1975 | Wada et al. ................. 428/461 |
| 3,933,779 | A | 1/1976 | Baron et al. ............... 260/93.5 |
| 3,941,746 | A | 3/1976 | Stephen et al. ............ 260/45.8 |
| 3,954,913 | A | 5/1976 | Uebele et al. ............... 260/880 |
| 4,039,491 | A | 8/1977 | Ikeda et al. ................. 260/875 |
| 4,134,895 | A | 1/1979 | Roth et al. .................. 260/326 |
| 4,134,927 | A | 1/1979 | Tomoshige et al. ......... 260/878 |
| 4,452,942 | A | 6/1984 | Shida et al. .................. 525/74 |
| 4,476,184 | A | 10/1984 | Lubowitz et al. ........... 428/288 |
| 4,503,219 | A | 3/1985 | Reffert et al. ............... 528/481 |
| 4,704,421 | A | 11/1987 | Teskin et al. ............... 524/287 |
| 4,739,017 | A | 4/1988 | Tabor et al. ................. 525/300 |
| 4,778,837 | A | 10/1988 | Waterman et al. ........... 524/89 |
| 4,801,637 | A | 1/1989 | McCullough et al. ...... 524/287 |
| 4,829,114 | A | 5/1989 | Trotoir et al. ............... 524/243 |
| 5,013,778 | A | 5/1991 | Bath et al. .................. 524/173 |
| 5,135,975 | A | 8/1992 | Rekers et al. ............... 524/108 |
| 5,491,187 | A | 2/1996 | Ward et al. ................. 524/159 |
| 5,922,793 | A | 7/1999 | Amos et al. ................ 524/159 |
| 5,929,146 | A | 7/1999 | Amos et al. ................. 524/89 |
| 6,096,811 | A | 8/2000 | Amos et al. ................. 524/89 |
| 6,465,551 | B1 * | 10/2002 | Zhao et al. ................. 524/284 |
| 6,521,685 | B1 * | 2/2003 | Zhao ........................... 524/396 |
| 6,534,574 | B1 * | 3/2003 | Zhao et al. ................. 524/284 |
| 6,559,211 | B1 * | 5/2003 | Zhao et al. ................. 524/285 |
| 6,583,206 | B1 * | 6/2003 | Zhao ........................... 524/242 |
| 6,585,819 | B1 * | 7/2003 | Zhao ......................... 106/162.1 |

FOREIGN PATENT DOCUMENTS

| DE | 1 544 851 | 5/1970 |
| DE | 1 694 914 B | 3/1972 |
| EP | 0267 695 | 5/1988 |
| EP | 0336 573 | 3/1989 |
| FR | 2 075 549 | 9/1971 |
| FR | 2 656 620 | 7/1991 |
| GB | 2 290 296 | 12/1995 |
| JP | 53-40760 | 4/1978 ................. 548/435 |
| JP | 57-18682 | 1/1982 |

(Continued)

OTHER PUBLICATIONS

H.N. Beck, "Heterogeneous Nucleating Agents of Polypropylene Crystallization", Journal of Applied Polymer Science, vol. 11, pp. 673-685, 1967.

(Continued)

*Primary Examiner*—Edward J. Cain
(74) *Attorney, Agent, or Firm*—Terry T. Moyer; John E. Vick, Jr.

(57) ABSTRACT

Bicyclic nucleator compounds that provide highly versatile nucleation benefits for different polyolefins are provided. Such nucleator compounds provide very high peak crystallization temperatures and significantly reduced crystallization cycle time for certain thermoplastic formulations with or without the presence of other calcium stearate and/or peroxide components within the same type of formulation. Furthermore, such inventive nucleator compounds exhibits very little if any fugitivity from such thermoplastic formulations thereby providing excellent processing characteristics as well as excellent nucleation capabilities for a variety of different thermoplastic resins, independent of the presence of different, potentially necessary, additives (such as calcium stearate). Thermoplastic compositions as well as thermoplastic additive packages comprising such inventive nucleator compounds are also contemplated within this invention.

10 Claims, No Drawings

FOREIGN PATENT DOCUMENTS

| | | |
|---|---|---|
| JP | 58-160343 | 9/1983 |
| JP | 61-17834 | 5/1986 |
| JP | 01-180514 | 7/1989 |
| JP | 03-076815 A | 4/1991 |
| JP | 05-139460 | 6/1993 |
| JP | 60-13837 | 1/1994 |
| JP | 07-173342 | 7/1995 |

OTHER PUBLICATIONS

Overman et al., "An Annual Publication of Satisfactory Methods for the Preparation of Organic Chemicals." Organic Synthesis, vol. 71, pp. 48-55, 1993.

Snider et al., "Mn(III)-Based Oxidative Free Radical Cyclization of Unsaturated Ketones," Journal of Organic Chemistry, vol. 60, pp. 5376-5377, 1995.

Fillon et al., "Self-Nucleation and Recrystallization of Isotactic Polypropylene (alpha Phase) Investigated by Differential Scanning Calorimetry," Journal of Polymer Science: Part B: Polymer Physics, vol. 31, pp. 1383-1393, 1993.

Fillon et al., "Self-Nucleation and Enhanced Nucleation of Polymers. Definition of a Convenient Calorimetric "Efficiency Scale" and Evaluation of Nucleating Additives in Isotactic Polypropylene (alpha phase)," Journal of Polymer Science: Part B: Polymer Physics, vol. 31 pp. 1395-1504, 1993.

\* cited by examiner

POLYMER ADDITIVE COMPOSITIONS COMPRISING HIGHLY VERSATILE THERMOPLASTIC NUCLEATORS

CROSS REFERENCE TO RELATED APPLICATIONS

This application is a continuation of application Ser. No. 09/864,460, filed on May 23, 2001 now U.S. Pat. No. 6,559,211. This parent application is herein entirely incorporated by reference.

FIELD OF THE INVENTION

This invention relates to types of bicyclic nucleator compounds that provide highly versatile nucleation benefits for different thermoplastics. Such nucleator compounds provide very high peak crystallization temperatures and short crystallization cycle time for certain thermoplastic formulations with or without the presence of other calcium stearate and/or peroxide components within the same type of formulation. Furthermore, such inventive nucleator compounds exhibit very little, if any, fugitivity from such thermoplastic formulations thereby providing excellent processing characteristics as well as excellent nucleation capabilities for a variety of different thermoplastic resins, independent of the presence of different, potentially necessary, additives (such as calcium stearate). Thermoplastic compositions as well as thermoplastic additive packages comprising such inventive nucleator compounds are also contemplated within this invention.

BACKGROUND OF THE PRIOR ART

All U.S. patents cited below are herein entirely incorporated by reference.

As used herein, the term "thermoplastic" is intended to mean a polymeric material that will melt upon exposure to sufficient heat but will retain its solidified state, but not prior shape without use of a mold or like article, upon sufficient cooling. Specifically, as well, such a term is intended solely to encompass polymers meeting such a broad definition that also exhibit either crystalline or semi-crystalline morphology upon cooling after melt-formation. Particular types of polymers contemplated within such a definition include, without limitation, polyolefins (such as polyethylene, polypropylene, polybutylene, and any combination thereof), polyamides (such as nylon), polyurethanes, polyesters (such as polyethylene terephthalate), and the like (as well as any combinations thereof).

Thermoplastics have been utilized in a variety of end-use applications, including storage containers, medical devices, food packages, plastic tubes and pipes, shelving units, and the like. Such base compositions, however, must exhibit certain physical characteristics in order to permit widespread use. Specifically within polyolefins, for example, uniformity in arrangement of crystals upon crystallization is a necessity to provide an effective, durable, and versatile polyolefin article. In order to achieve such desirable physical properties, it has been known that certain compounds and compositions provide nucleation sites for polyolefin crystal growth during molding or fabrication. Generally, compositions containing such nucleating compounds crystallize at a much faster rate than unnucleated polyolefin. Such crystallization at higher temperatures results in reduced fabrication cycle times and a variety of improvements in physical properties, such as, as one example, stiffness.

Such compounds and compositions that provide faster and or higher polymer crystallization temperatures are thus popularly known as nucleators. Such compounds are, as their name suggests, utilized to provide nucleation sites for crystal growth during cooling of a thermoplastic molten formulation. Generally, the presence of such nucleation sites results in a larger number of smaller crystals. As a result of the smaller crystals formed therein, clarification of the target thermoplastic may also be achieved, although excellent clarity is not always a result. The more uniform, and preferably smaller, the crystal size, the less light is scattered. In such a manner, the clarity of the thermoplastic article itself can be improved. Thus, thermoplastic nucleator compounds are very important to the thermoplastic industry in order to provide enhanced clarity, physical properties and/or faster processing.

As an example of one type of nucleator, dibenzylidene sorbitol derivative compounds are typical nucleator compounds, particularly for polypropylene end-products. Compounds such as 1,3-O-2,4-bis(3,4-dimethylbenzylidene) sorbitol, available from Milliken Chemical under the trade name Millad® 3988 (hereinafter referred to as 3,4-DM-DBS), provide excellent nucleation characteristics for target polypropylenes and other polyolefins. Other well known compounds include sodium benzoate, sodium 2,2'-methylene-bis-(4,6-di-tert-butylphenyl) phosphate (from Asahi Denka Kogyo K.K., known as and hereinafter referred to as NA-11), aluminum bis[2,2'-methylene-bis-(4,6-di-tert-butylphenyl)phosphate] (also from Asahi Denka Kogyo K.K., which is understood to be known as and hereinafter referred to as NA-21), talc, and the like. Such compounds all impart high polyolefin crystallization temperatures; however, each also exhibits its own drawback for large-scale industrial applications.

Other acetals of sorbitol and xylitol are typical nucleators for polyolefins and other thermoplastics as well. Dibenzylidene sorbitol (DBS) was first disclosed in U.S. Pat. No. 4,016,118 by Hamada, et al. as effective nucleating and clarifying agents for polyolefin. Since then, large numbers of acetals of sorbitol and xylitol have been disclosed, including bis(p-methylbenzylidene) sorbitol (hereinafter referred to as 4-MDBS). Representative references of such other compounds include Mahaffey, Jr., U.S. Pat. No. 4,371,645 [diacetals of sorbitol having at least one chlorine or bromine substituent].

As noted above, another example of the effective nucleating agents are the metal salts of organic acids. Wijga in U.S. Pat. Nos. 3,207,735, 3,207,736, and 3,207,738, and Wales in U.S. Pat. Nos. 3,207,737 and 3,207,739, suggest that aliphatic, cycloaliphatic, and aromatic carboxylic, dicarboxylic or higher polycarboxylic acids, and corresponding anhydrides and metal salts, are effective nucleating agents for polyolefin. They further state that benzoic acid type compounds, in particular sodium benzoate, are the best nucleating agents for their target polyolefins.

Another class of nucleating agents was suggested by Nakahara, et al. in U.S. Pat. No. 4,463,113, in which cyclic bis-phenol phosphates was disclosed as nucleating and clarifying agents for polyolefin resins, as well as U.S. Pat. No. 5,342,868 to Kimura, et al. Compounds that are based upon these technologies are marketed under the trade names NA-11 and NA-21, discussed above.

Furthermore, a certain class of bicyclic compounds, such as bicyclic dicarboxylic acid and salts, have been taught as polyolefin nucleating agents as well within Patent Cooperation Treaty Application WO 98/29494, 98/29495 and 98/29496, all assigned to Minnesota Mining and Manufacturing. The best working examples of this technology are embodied in disodium bicyclo[2.2.1]heptene dicarboxylate and camphanic acid.

The efficacy of nucleating agents is typically measured by the peak crystallization temperature of the polymer compositions containing such nucleating agents. A high polymer peak crystallization is indicative of high nucleation efficacy, which generally translates into fast processing cycle time and more desirable physical properties, such as stiffness/impact balance, etc., for the fabricated parts. Compounds mentioned above all impart relatively high polyolefin crystallization temperatures; however, each also exhibits its own drawback for large-scale industrial applications.

For example, it is very desirable that the effective nucleating compounds exhibit a very high peak crystallization temperature, for example, above 125° C. within a test homopolymer polypropylene that, when unnucleated exhibits a number of different characteristics such as a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93° (which provides a homopolymer exhibiting an isotacticity of between about 96 and 99%), wherein said peak crystallization temperature is measured by differential scanning calorimetry in accordance with ASTM Test Method D3417-99 modified to measure at heating and cooling rates of 20° C./minute. Such a polypropylene homopolymer provides an effective test subject for this purpose due to the general uniformity of product available (and thus better uniformity in peak crystallization temperature, etc., results, therein for samples of such a thermoplastic), as well as the widespread use of such a thermoplastic. Of course, it should be well understood by the ordinarily skilled artisan that such a test homopolymer is not the only thermoplastic in which the inventive nucleating agent may be present; it is solely a test formulation in order to determine the highest peak crystallization temperature, etc., for certain inventive nucleating agents under certain conditions. Of the nucleating agents mentioned above, only camphanic acid exhibits such a high polymer peak crystallization temperature within such a test homopolymer propylene formulation. However, as shown in the comparative examples within this invention, camphanic acid exhibits very poor thermal stability, where it tends to vaporize and accumulate on the surface of plastic processing equipments during processing. This phenomenon is generally referred to as "plate out" within the plastics industry. The "plate out" effect of this additive make it impractical for any commercial use. Thus, the combination of very high polymer peak crystallization temperature (thus highly efficient nucleation) and a low degree of fugitivity (and thus high thermal stability and low plate-out characteristics) within the target polymers (e.g., preferably polyolefins such as polypropylene) is very desirable within the plastics industry, particularly where the peak crystallization temperature is measured above 126° C. within a homopolymer polypropylene measured by differential scanning calorimetry at a rate of 20° C./minute. So far, such a combination has not been provided within this intensively studied area of polymer nucleating agents.

Beyond high polymer crystallization temperature and low fugitivity, there are a number of other performance characteristics important for the practical use of such nucleating agents. For example, one of great interest is the compatibility of such compounds with different additives widely used within typical polyolefin (e.g., polypropylene, polyethylene, and the like) plastic articles. As noted previously, calcium stearate compatibility is particularly important. Unfortunately, most of the nucleator compounds noted above (such as sodium benzoate, NA-11, disodium bicyclo[2.2.1]heptene dicarboxylate) exhibit deleterious nucleating efficacy when present with such compounds within polyolefin articles. It is generally speculated that the calcium ion from the stearate transfers positions with the sodium ions of the nucleating agents, rendering the nucleating agents ineffective for their intended function. As a result, such compounds sometimes exhibit unwanted plate-out characteristics and overall reduced nucleation performance as measured, for example, by a decrease in crystallization temperature during and after polyolefin processing of greater than 2° C. as compared to the peak crystallization temperature of the nucleated polymer with no calcium stearate present therein. In order to avoid combinations of these standard nucleators and calcium salts, other nonionic acid neutralizers, such as dihydrotalcite (DHT4-A), would be necessary for use in conjunction with such nucleators. Such a combination, however, has proven problematic in certain circumstances due to worsened aesthetic characteristics (e.g., higher haze), and certainly higher costs in comparison with standard calcium salts.

Other problems encountered with the standard nucleators noted above include inconsistent nucleation due to dispersion problems, resulting in stiffness and impact variation in the polyolefin article. Substantial uniformity in polyolefin production is highly desirable because it results in relatively uniform finished polyolefin articles. If the resultant article does not contain a well dispersed nucleating agent, the entire article itself may suffer from a lack of rigidity and low impact strength.

Furthermore, storage stability of nucleator compounds and compositions is another potential problem with thermoplastic nucleators and thus is of enormous importance. Since nucleator compounds are generally provided in powder or granular form to the polyolefin manufacturer, and since uniform small particles of nucleating agents are imperative to provide the requisite uniform dispersion and performance, such compounds must remain as small particles through storage. Certain nucleators, such as sodium benzoate, exhibit high degrees of hygroscopicity such that the powders made therefrom hydrate easily resulting in particulate agglomeration. Such agglomerated particles may require further milling or other processing for deagglomeration in order to achieve the desired uniform dispersion within the target thermoplastic. Furthermore, such unwanted agglomeration due to hydration may also cause feeding and/or handling problems for the user.

Some nucleating agents, such as certain DBS derivatives, exhibit certain practical deficiencies such as a tendency to plate-out at high processing temperatures. DBS derivatives, particularly where the aromatic rings are mono-substituted, show much improved thermal stability. However, such compounds also tend to exhibit undesirable migratory properties coupled with problematic organoleptic deficiencies within certain polyolefin articles. As a result, such compounds cannot be widely utilized in some important areas, such as within medical devices (e.g., syringes, and the like) and food packaging.

These noticeable problems have thus created a long-felt need in the plastics industry to provide such compounds that do not exhibit the aforementioned problems and provide excellent peak crystallization temperatures and low fugitivity for the target polyolefins themselves. To date, the best compounds for this purpose remain those noted above. To date, nucleators exhibiting exceptionally high peak crystallization temperatures, low fugitivity, low hygroscopicity, excellent thermal stability, and non-migratory properties within certain target polyolefins, and compatibility with most standard polyolefin additives (such as, most importantly, calcium stearate) have not been available to the plastics industry.

OBJECTS OF THE INVENTION

Therefore, an object of the invention is to provide a polyolefin nucleating agent that provides excellent high peak crystallization temperatures to polypropylene articles and formulations and also exhibits extremely low fugitivity (excellent thermal stability, low plate-out). A further object of the invention is to provide a nucleator compound and compositions thereof that exhibit excellent calcium stearate compatibility within target polyolefin articles and formulations. Also, the inventive compounds must exhibit excellent low hygroscopicity in order to accord an extremely good shelf-stable additive composition. Another objective of this invention is to provide a nucleating compound and composition that exhibits low migration once incorporated within polyolefin articles. Another objective of this invention is to provide a nucleating agent and composition that exhibits little or no foul taste and/or odor within polyolefin articles. Another object of the invention is to provide a nucleator compound that affects the crystallization process within the target polyolefin polymer in such a manner that the resultant lamellar structure is highly unique (extremely thick) in comparison with other nucleated polypropylene articles and formulations such that said polyolefin exhibits very high stiffness properties. Additionally, it is an object of this invention to provide a nucleator compound or composition that may be used in various polyolefin media for use in myriad end-uses.

Accordingly, this invention encompasses a nucleating agent which induces a peak crystallization temperature of at least 125° C. (preferably, at least 125.5; more preferably, at least 126; still more preferably, at least 126.5; and most preferably at least 127; preferably such a temperature is as high as possible, up to the level of a self-nucleated test homopolymer polypropylene resin, such as at about 137–8° C., with a high temperature of about 134° C. most preferred) for a test homopolymer polypropylene formulation, wherein the unnucleated test homopolymer propylene exhibits a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93°, and wherein said formulation is extruded then molded into plaques having dimensions of about 51 mm×76 mm×1.27 mm, wherein said peak crystallization temperature is measured by differential scanning calorimetry in accordance with a modified ASTM Test Method D3417-99 at heating and cooling rates of 20° C./minute, and wherein said nucleating agent also exhibits no appreciable fugitivity from said test homopolymer polypropylene formulation during compounding of said test homopolymer polypropylene formulation.

Also encompassed within this invention is a nucleating agent which induces a crystallization half time ($t_{1/2}$) of at most 2.0 minutes in a test homopolymer polypropylene formulation, wherein the unnucleated test homopolymer propylene exhibits a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93° C., and wherein said formulation is extruded then molded into plaques having dimensions of about 51 mm×76 mm×1.27 mm, wherein said $t_{1/2}$ is measured by differential scanning calorimetry at a constant crystallization temperature of about 140° C., and wherein said nucleator also exhibits no appreciable fugitivity from said polypropylene formulation.

Additionally, this invention also encompasses a nucleating agent which induces a standard peak crystallization temperature of at least 123.5° C. in a test homopolymer polypropylene formulation, wherein the unnucleated test homopolymer polypropylene exhibits a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93° C., and wherein said formulation is extruded then molded into plaques having dimensions of about 51 mm×76 mm×1.27 mm, wherein said peak crystallization temperature measured by differential scanning calorimetry in accordance with a modified ASTM Test Method D3417-99 at heating and cooling rates of 20° C./minute and wherein said nucleating agent is present in at most 1500 ppm, wherein said polymer nucleator exhibits no appreciable fugitivity from said polypropylene formulation during compounding of said polypropylene, and wherein said nucleating agent induces said peak crystallization temperature in said polypropylene formulation when no calcium stearate is present, and wherein said nucleating agent induces a comparative peak crystallization temperature of at most 2° C. lower than said standard peak crystallization for the same polypropylene formulation when at least 800 ppm of calcium stearate is present. Furthermore, such a compound exhibits a very low hygroscopicity as well.

Additionally, this invention encompasses a nucleating agent which produces an effective nucleation density of greater than $7 \times 10^9$ nuclei/cm$^3$ at an isothermal crystallization temperature of about 148° C. in a test homopolymer polypropylene formulation comprising said nucleating agent, wherein the unnucleated test homopolymer propylene exhibits a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93°, and wherein said formulation is extruded then molded into plaques having dimensions of about 51 mm×76 mm×1.27 mm, and wherein said nucleating agent also exhibits no appreciable fugitivity from said test homopolymer polypropylene formulation during compounding of said test homopolymer polypropylene formulation comprising said nucleating agent.

Still further encompassed within this invention is a nucleating agent which exhibits a nucleation effectiveness factor (NEF) of greater than 0.06 in a test homopolymer polypropylene formulation having a density of about 0.9 g/cc, a melt flow of about 12 g/l 10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature of 0.46 mPa at about 93° C., wherein said formulation is extruded and then molded into plaques having dimensions of about 51 mm×76 mm×1.27 mm.

It should also be well understood and appreciated by one of ordinary skill within this art that the inventive nucleating agent is defined above as performing to a certain degree within a test polymer formulation, and is not required to be a component within such a test polymer formulation. Thus, although such an inventive nucleating agent must perform to a certain level within a test homopolymer propylene, it may be present within any other type of polymer (such as a thermoplastic), including blends of polymers. The particular polymers within which such an inventive nucleating is effective and useful are listed below in greater detail.

The bicyclic compounds are defined as organic compounds that contain two or more rings wherein at least two of the said rings share at least two nonadjacent atoms.

Some particular, non-limiting examples of such novel nucleator compounds include the metal or organic salts of saturated [2.2.1] bicyclic dicarboxylates, and most preferably of these types of compounds conforming to Formula (I)

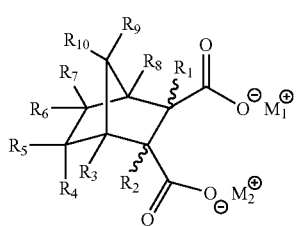

(I)

wherein $M_1$ and $M_2$ are the same or different and are independently selected from the group consisting of metal or organic cations, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxyl, $C_1$–$C_9$ alkoxy, $C_1$–$C_9$ alkyleneoxy, amine, and $C_1$–$C_9$ alkylamine, halogen, phenyl, alkylphenyl, and geminal or vicinal $C_1$–$C_9$ carbocyclic. Preferably, the metal cations are selected from the group consisting of calcium, strontium, barium, magnesium, aluminum, silver, sodium, lithium, rubidium, potassium, and the like. Within that scope, group I and group II metal ions are generally preferred. Among the group I and II cations, sodium, potassium, calcium and strontium are preferred, wherein sodium and calcium are most preferred. Furthermore, the $M_1$ and $M_2$ groups may also be combined to form a single metal cation (such as calcium, strontium, barium, magnesium, aluminum, and the like). Although this invention encompasses all stereochemical configurations of such compounds, the cis configuration is preferred wherein cis-endo is the most preferred embodiment. The preferred embodiment polyolefin articles and additive compositions for polyolefin formulations comprising at least one of such compounds are also encompassed within this invention.

The term "no appreciable fugitivity" as used as one description within this invention is intended to encompass nucleators which exhibit very high heat stabilities (and thus very low plate-out) within test polypropylene formulations. Therefore, a weight loss of nucleator compound during a thermal stability test of at most 5% is encompassed within this term. Such thermal stability testing is described in greater detail below.

DETAILED DESCRIPTION OF THE INVENTION

As noted above, in order to develop a proper polyolefin nucleator compound or composition for industrial applications, a number of important criteria need to be met. The inventive nucleating agents meet all of these important requirements very well. For instance, as discussed in greater detail below, these inventive salts provide excellent high peak crystallization temperatures in a variety of polyolefin formulations, particularly within random copolymer polypropylene (hereinafter RCP) and homopolymer polypropylene (hereinafter HP). As a result, such inventive salts provide excellent mechanical properties for polyolefin articles without the need for extra fillers and rigidifying additives, and desirable processing characteristics such as improved (shorter) cycle time. The salts also show much improved hygroscopicity comparing to prior art and thus granular or powder formulations of such a salt do not agglomerate or clump together. Lastly, such inventive salts do not interact deleteriously with calcium stearate additives.

Such properties are highly unexpected and unpredictable, particularly in view of the closest prior art, the WO 98/29494 reference discloses nucleation and clarification additives for polyolefin articles including unsaturated [2.2.1]dicarboxylate salts; however, there is no exemplification of a saturated dicarboxylate salt of this type. The closest embodiment within that art is identified as disodium bicyclo[2.2.1]heptene dicarboxylate. After intensive investigations, it has been determined that, quite unexpectedly, as discussed below in greater detail, the hydrogenation of such compounds provides vastly improved nucleation efficacy for the inventive compounds and within the inventive polyolefin compositions. It has now been found that the saturation of Diels-Alder reaction products to form dicarboxylate salts, and in particular, without intending to limit the scope of the invention, saturated bicyclic dicarboxylate salts, provide unforeseen benefits for polyolefin nucleation processes.

As indicated in Table 1, below, the peak crystallization temperatures provided target polyolefin articles with these inventive saturated compounds are from about 2.5 to about 5° C. above that for the related unsaturated compounds. Such dramatic improvements are simply unexpected and are unpredictable from any known empirical or theoretical considerations. Furthermore, significant improvements in hygroscopicity of the saturated compounds were also unexpectedly observed. Such unpredictable improvements are of great practical significance as discussed before.

Yet another surprise was the improved compatibility between these inventive saturated compounds and typical acid scavenger salt compounds utilized within polyolefin formulations and articles, such as calcium and lithium stearate. Such compatibility, coupled with the high peak crystallization temperatures available from the inventive compounds, thus provides a highly desirable thermoplastic nucleator compound. Furthermore, the ability to provide extremely high nucleation density measurements (above an order of magnitude than typical nucleating agents at various isothermal crystallization temperatures) is highly desirable and previously unattainable as well.

The inventive salts are thus added within the target polyolefin in an amount from about 50 ppm to about 20,000 ppm by weight in order to provide the aforementioned beneficial characteristics, most preferably from about 200 to about 4000 ppm. Higher levels, e.g., 50% or more by weight, may also be used in a masterbatch formulation. Optional additives within the inventive salt-containing composition, or within the final polyolefin article made therewith, may include plasticizers, antistatic agents, stabilizers, ultraviolet absorbers, and other similar standard polyolefin thermoplastic additives. Other additives may also be present within this composition, most notably antioxidants, antistatic compounds, antimicrobials (preferably silver-based ion-exchange compounds, such as ALPHASAN® antimicrobials available from Milliken & Company), perfumes, chlorine scavengers, and the like. Such additives, and others not listed, are well known to those skilled in the art.

The term polyolefin or polyolefin resin is intended to encompass any materials comprised of at least one polyolefin compound. Preferred examples include isotactic and syndiotactic polypropylene, polyethylene, poly(4-methyl) pentene, polybutylene, and any blends or copolymers thereof, whether high or low density in composition. The polyolefin polymers of the present invention may include aliphatic polyolefins and copolymers made from at least one aliphatic olefin and one or more ethylenically unsaturated co-monomers. Generally, the co-monomers, if present, will be provided in aminor amount, e.g., about 10 percent or less or even about 5 percent or less, based upon the weight of the polyolefin (e.g. random copolymer polypropylene), but copolymers containing up to 25% or more of the co-monomer (e.g., impact copolymers) are also envisaged. Other polymers or rubber (such as EPDM or EPR) may also be compounded with the polyolefin to obtain the aforementioned characteristics. Such co-monomers may serve to assist in clarity improvement of the polyolefin, or they may function to improve other properties of the polymer. Other examples include acrylic acid and vinyl acetate, etc. Examples of olefin polymers whose transparency can be improved conveniently according to the present invention are polymers and copolymers of aliphatic monoolefins containing 2 to about 6 carbon atoms which have an average molecular weight of from about 10,000 to about 2,000,000, preferably from about 30,000 to about 300,000, such as, without limitation, polyethylene, linear low density polyethylene, isotactic polypropylene, syndiotactic polypropylene, crystalline ethylene propylene copolymer, poly(1-butene), polymethylpentene, 1-hexene, 1-octene, and vinyl cyclohexane. The polyolefins of the present invention may be described as basically linear, regular polymers that may optionally contain side chains such as are found, for instance, in conventional low density polyethylene.

Although polyolefins are preferred, the nucleating agents of the present invention are not restricted to polyolefins, and may also give beneficial nucleation properties to polyesters such as polyethylene terephthalate (PET), polybutylene terephthalate (PBT), and polyethylene naphthalate (PEN), as well as polyamides such as Nylon 6, Nylon 6,6, and others. Generally, any thermoplastic composition having some crystalline content may be improved with the nucleating agents of the present invention.

The compositions of the present invention may be obtained by adding the inventive saturated bicyclic dicarboxylic salt (or combination of salts or composition comprising such salts) to the thermoplastic polymer or copolymer and merely mixing the resultant composition by any suitable means. Alternatively, a concentrate containing as much as about 20 percent by weight of the inventive saturated [2.2.1] salt in a polyolefin masterbatch comprising the required acid scavenger may be prepared and be subsequently mixed with the target resin. Furthermore, the inventive compositions (with other additives potentially) may be present in any type of standard thermoplastic (e.g., polyolefin, most preferably) additive form, including, without limitation, powder, prill, agglomerate, liquid suspension, and the like, particularly comprising dispersion aids such as polyolefin (e.g., polyethylene) waxes, stearate esters of glycerin, montan waxes, mineral oil, and the like. Basically, any form may be exhibited by such a combination or composition including such combination made from blending, agglomeration, compaction, and/or extrusion.

The composition may then be processed and fabricated by any number of different techniques, including, without limitation, injection molding, injection blow molding, injection stretch blow molding, injection rotational molding, extrusion, extrusion blow molding, sheet extrusion, film extrusion, cast film extrusion, foam extrusion, thermoforming (such as into films, blown-films, biaxially oriented films), thin wall injection molding, and the like into a fabricated article.

PREFERRED EMBODIMENTS OF THE INVENTION

Examples of particularly preferred fluid dispersions within the scope of the present invention are presented below.

Production of Inventive Salts

EXAMPLE A

Disodium bicyclo[2.2.1]heptane-2,3-dicarboxylate

To a solution of disodium bicyclo[2.2.1]hept-5-ene-2,3-dicarboxylate (10.0 g, from example 3) in water (100 g) was added 0.5 g palladium on activated carbon (5 wt %). The mixture was transferred into a Parr reactor and was subjected to hydrogenation (50 psi, room temperature) for 8 hours. The activated carbon was filtered out. Water is removed in vacuo at 75° C. The resulting product was dried and milled (m.p >300° C.).

EXAMPLE 2

Calcium bicyclo[2.2.1]heptane-2,3-dicarboxylate

To a solution of disodium bicyclo[2.2.1]heptane-2,3-dicarboxylate (22.6 g, 0.1 mol) in water (150 g) was added a solution of calcium chloride dihydrate (14.7 g, 0.1 mol) in water (100 g). The mixture stirred at 60° C. for 2 hours. The resulting white precipitate was filtered. The white powdery product was dried and milled (m.p. >300° C.).

EXAMPLE 3 (Comparative)

Disodium bicyclo[2.2.1]hept-5-ene-2,3-dicarboxylate

To a suspension of endo-bicyclo[2.2.1]hept-5-ene-2,3-dicarboxylic anhydride (16.4 g, 0.1 mol) in water (100 g) was added sodium hydroxide (8.0 g, 0.2 mol) at room temperature. The mixture was then stirred at 80° C. for 2 hour. A clear, homogeneous solution was obtained. Water was removed in vacuo at 75° C. and the resulting white crystalline product was dried and milled (m.p >300° C.).

Other lithium, rubidium, potassium, strontium, barium, and magnesium [2.2.1]heptane dicarboxylate salts were also prepared in like manners for testing. Commercial samples of NA-11, NA-21, 3,4-DMDBS, and 4-MDBS were used in this evaluation without further purification and treatment.

Camphanic acid (purity higher than 98%) was purchased from Aldrich Chemical company. It was used without further purification and treatment.

Nucleation Efficacy Tests

Thermoplastic compositions (plaques) were produced comprising the additives from the Examples above and sample homopolymer polypropylene (HP) resin plaques, produced dry blended in a Welex mixer at ~2000 rpm, extruded through a single screw extruder at 400–450° F., and pelletized. Accordingly, one kilogram batches of target polypropylene were produced in accordance with the following table:

HOMOPOLYMER POLYPROPYLENE COMPOSITION

| Component | Amount |
|---|---|
| Polypropylene homopolymer (Himont Profax ® 6301) | 1000 g |
| Irganox ® 1010, Primary Antioxidant (from Ciba) | 500 ppm |
| Irgafos ® 168, Secondary Antioxidant (from Ciba) | 1000 ppm |
| Acid Scavenger | as noted |
| Nucleating Agent | as noted |

The base HP [having a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93° C., as well as an expected isotacticity of between about 96 and 99% through xylene solubles analysis] and all additives were weighed and then blended in a Welex mixer for 1 minute at about 1600 rpm. All samples were then melt compounded on a Killion single screw extruder at a ramped temperature from about 204° to 232° C. through four heating zones. The melt temperature upon exit of the extruder die was about 246° C. The screw had a diameter of 2.54 cm and a length/diameter ratio of 24:1. Upon melting the molten polymer was filtered through a 60 mesh (250 micron) screen. Plaques of the target polypropylene were then made through extrusion into an Arburg 25 ton injection molder. The molder was set at a temperature anywhere between 190 and 260° C., with a range of 190 to 240° C. preferred, most preferably from about 200 to 230° C. and at an injection speed within the range of between about 1 and about 5 cm³/second. The plaques had dimensions of about 51 mm×76 mm×1.27 mm, and the mold had a mirror finish which was transferred to the individual plaques. The mold cooling circulating water was controlled at a temperature of about 25° C.

Testing for nucleating effects and other important criteria were accomplished through the formation of plaques of clarified polypropylene thermoplastic resin. These plaques were formed through the process outlined above with the specific compositions listed above in the above Table.

These plaque formulations are, of course, merely preferred embodiments of the inventive article and method and are not intended to limit the scope of this invention. The resultant plaques were then tested for peak crystallization temperatures (by Differential Scanning Calorimetry). Crystallization is important in order to determine the time needed to form a solid article from the molten polyolefin composition. Generally, a polyolefin such as polypropylene has a crystallization temperature of about 110° C. at a cooling rate of 20° C./min. In order to reduce the amount of time needed to form the final product, as well as to provide the most effective nucleation for the polyolefin, the best nucleator compound added will invariably also provide the highest crystallization temperature for the final polyolefin product. The nucleation composition efficacy, particular polymer peak crystallization temperature ($T_c$), was evaluated by using a modified differential scanning procedure based upon the test protocol ASTM D3417-99 wherein the heating and cooling rates utilized have been altered to 20° C./minute each. Thus, to measure the peak crystallization temperatures of the samples, the specific polypropylene compositions were heated from 60° C. to 220° C. at a rate of 20° C. per minute to produce molten formulations and held at the peak temperature for 2 minutes. At that time, the temperature was then lowered at a rate of 20° C. per minute until it reached the starting temperature of 60° C. for each individual sample. The important crystallization temperatures were thus measured as the peak maxima during the individual crystallization exotherms for each sample. After allowing the plaques to age for 24 hours at room temperature, haze values were measured according to ASTM Standard Test Method D1003-61 "Standard Test Method for Haze and Luminous Transmittance of Transparent Plastics" using a BYK Gardner Hazegard Plus.

The following Table lists the peak crystallization temperatures and haze results for the sample plaques prepared with the additives noted above (with certain acid scavengers and levels thereof as well as levels of nucleating agent used therein specified for each sample; Samples 5–10, below included 2500 ppm each of the nucleating agent):

EXPERIMENTAL TABLE 1

Performance of Bicyclic Nucleators in Polypropylene Homopolymer

| Sample # | Nucleator Conc. (ppm) | Peak $T_c$ (° C.) | Haze (%) |
|---|---|---|---|
| 1 | Example A (1000 ppm)[a] | 126 | 34 |
| 2 | Example A (2500 ppm)[a] | 128 | 30 |
| 3 | Example B (1000 ppm)[a] | 125 | 48 |
| 4 | Example B (2500 ppm)[a] | 127 | 45 |
| 5 | Lithium bicyclo[2.2.1]heptane dicarboxylate[a] | 123 | 56 |
| 6 | Potassium bicyclo[2.2.1]heptane dicarboxylate[b] | 125 | 67 |
| 7 | Rubidium bicyclo[2.2.1]heptane dicarboxylate[b] | 123 | 55 |
| 8 | Magnesium bicyclo[2.2.1]heptane dicarboxylate[a] | 117 | 78 |
| 9 | Barium bicyclo[2.2.1]heptane dicarboxylate[a] | 121 | 71 |
| 10 | Strontium bicyclo[2.2.1]heptane dicarboxylate[a] | 124 | 56 |
| 11 | - - - (Comparative Control)[a] | 110 | 68 |
| 12 | Example C (Comparative) (1000 ppm)[a] | 122 | 50 |
| 13 | Example C (Comparative) (2500 ppm)[a] | 123 | 46 |
| 14 | 3,4-DMDBS (2500 ppm)[a] | 123 | 11 |
| 15 | NA-11 (1000 ppm)[c] | 124 | 32 |
| 16 | NA-21 (2500 ppm)[a] | 123 | 20 |
| 17 | Camphanic Acid (2500 ppm)[b] | 127 | 30 |

[a]Including 800 ppm of calcium stearate acid scavenger
[b]Including 800 ppm of lithium stearate acid scavenger
[c]Including 400 ppm of DHT-4A acid scavenger The data show that inventive nucleating agents in Examples A and B, above, exhibit significantly high polymer peak crystallization temperatures and simultaneous low haze measurements.

Another important test for nucleation efficacy is the crystallization half-time ($t_{1/2}$). This measurement was conducted on DSC where the specific polypropylene composition was heated from 60° C. to 220° C. at a rate of 20° C. per minute to produce a molten formulation and held at the peak temperature for 2 minutes. At that time, the temperature was then lowered quickly to 140° C., where the sample was held. The exotherm of crystallization was measured with time. The time where exactly one-half of the heat of crystallization is generated was recorded as the crystallization half time. Shorter crystallization half time is indicative of higher nucleation efficacy. In a practical sense, a shorter crystallization half time is an indicator of a shorter cycle time, and thus of significant value.

EXPERIMENTAL TABLE 2

Crystallization Half Time in Homopolymer

| Sample # (from Experimental Table 1) | Loading (ppm) | $t_{1/2}$ (minutes) |
|---|---|---|
| 13 (Comparative) | 2500 | 4.50 |
| 2 | 2500 | 0.98 |
| 4 | 2500 | 1.40 |

The data show that the inventive compounds of Examples A and B exhibit significantly shorter crystallization half times.

Thermal Stability (Fugitivity) Test

Thermal stability of is an important criteria for polymer additives. Additives lacking thermal stability would cause plate out and other processing issues. Stability tests are conducted on a Thermogravimetric Analyzer from TA Instruments. Roughly 10 mg of dry sample is added to the stainless steel sample cell. The sample cell is then blanketed with nitrogen. Sample is allowed to equilibrate for 5 minutes at 25° C. The temperature is then raised at 20° C./min ramp rate until it reaches 500° C. Weight loss in percentage versus temperature is recorded for the sample nucleator from within the sample polypropylene as a result of such thermal stability testing. Polypropylene is typically processed between 200–250° C. and a weight loss of the sample nucleator in excess of 5% at 250° C. is generally considered as unsuitable for use since the remaining amounts would be insufficient for proper and necessary nucleation to occur. The weight loss data for camphanic acid and disodium [2.2.1]cycloheptane dicarboxylate is shown below:

EXPERIMENTAL TABLE 3

Thermal Stability Results

| Temperature | % Weight loss of Example A | % weight loss of Camphanic acid |
|---|---|---|
| 200° C. | 0.9% | 10% |
| 250° C. | 1.2% | 47% |
| 300° C. | 1.4% | 89% |

The data indicate that although camphanic acid exhibits comparable polymer peak crystallization temperature, it lacks the necessary thermal stability for practical commercial use.

Calcium Stearate Compatibility Test

In this test, the nucleators were tested in formulations with and without calcium stearate. The nucleation efficacy of the nucleators in each formulation was studied by measuring polymer crystallization temperature. The formulations and testing conditions are identical with those discussed above. A drop of 2° C. or more is considered a failure.

EXPERIMENTAL TABLE 4

Calcium Stearate (CaSt) Compatibility Test

| Sample # | Nucleator Conc. (ppm) | CaSt Loading (ppm) | Peak $T_c$ | Peak $T_c$ Change |
|---|---|---|---|---|
| 18 | Example A (2500 ppm)$^d$ | 0 | 128 | — |
| 19 | Example A (2500 ppm)$^e$ | 800 | 128 | ~0 |
| 20 | Example B (2500 ppm)$^d$ | 0 | 127 | — |
| 21 | Example B (2500 ppm)$^e$ | 800 | 127 | ~0 |
| 22 | NA-11$^d$ | 0 | 124 | — |
| 23 | NA-11$^e$ | 800 | 121 | 3 |
| 24 | Example C$^d$ | 0 | 123 | — |
| 25 | ExampleC$^e$ | 800 | 121 | 2 |
| 26 | Camphanic Acid$^f$ | 0 | 127 | — |
| 27 | Camphanic Acid$^e$ | 800 | 124 | 3 |

$^d$Including 400 ppm of DHT-4A acid scavenger
$^e$Having calcium stearate as the only acid scavenger present
$^f$Including 800 ppm of lithium stearate acid scavenger (lithium stearate is a poor acid scavenger and is thus utilized with camphanic acid in order not to scavenge the camphanic acid itself from the formulation)

The data show that the inventive nucleators in Examples A and Example B pass the compatibility test with calcium stearate.

Hygroscopicity Test:

These tests were carried out on the milled products to give adequate surface area for moisture uptake. Two grams of each example were spread out on a watch glass and weighed immediately after drying in a vacuum oven. The samples were then placed in a controlled humidity (65%) environment and the weight was taken each day for 7 days. The percent weight gain was defined as the percent moisture uptake. Experimental Table 5 below summarizes the results:

EXPERIMENTAL TABLE 5

Hygroscopicity Test Data

| Sample # | Nucleating Agent | Weight Gain (% w/w) |
|---|---|---|
| 28 | Example A | 1% |
| 29 | Example B | 0% |
| 30 | Example C (Comparative) | 8% |

It is clear from the above data that saturation of Example 3 reduces the hygroscopicity over that of the prior art significantly, and the use of calcium as the metal reduces the moisture uptake to zero.

Nucleation Efficacy in Polyester:

The inventive additives were also tested as nucleating agents for polyester. Additives were compounded with a C. W. Brabender Torque Rheometer at 5000 ppm into Shell Cleartuff™ 8006 PET bottle grade resin having an Intrinsic Viscosity of 0.80. All resin was dried to less than 20 ppm water. Samples were taken, pressed, and rapidly cooled into 20–40 mil films. All samples were dried at 150° C. under vacuum for 6 hours prior to analysis. The samples were analyzed under nitrogen on a Perkin Elmer System 7 differential scanning calorimeter using a heating and cooling rate of 20° C./min. The polymer peak crystallization temperature was measured as described before. The data is shown in Experimental Table 6 below:

EXPERIMENTAL TABLE 6

Polyester Nucleating Results

| Sample | Peak Cryst. Temp. (° C.) |
|---|---|
| Control | 155 |
| Example C | 184 |
| Example A | 194 |

Thus, the inventive saturated compound exhibited much improved nucleation of polyester over the control with no nucleator compound and the unsaturated nucleator compound.

Retort Extraction Test:

Plaques, as prepared above, were subjected an extraction test as outlined in the following procedure:

Seven plaques were cut into nine strips each to give a total surface area of approximately 600 cm$^2$. These strips were rinsed with deionized water and allowed to dry. They were then placed into a glass extraction vessel and covered with 200 ml of deionized water. The glass vessels and their contents were autoclaved for 60 minutes at 120° C., and were allowed to cool and settle for 24 hours. After settling, approximately 60 ml of the extraction solution was transferred to a clean beaker, and 10 ml of this solution was filtered through a 0.8-μm filter fitted to a syringe. The filtrate was collected in a 1-cm quartz cuvette. The cuvette and contents were scanned for peak UV absorbances in the wavelength range 220–240 nm and 241–350 nm, after a suitable deionized water blank had been scanned. Such a test provides indications of the effectiveness of the resultant thermoplastic with regards to the extractability of any contents of the plastic itself and thus is a good indicator as to the usefulness of the thermoplastic product for different types of end-uses. The lower the extraction level, the more useful such thermoplastic is for food contact, for example.

EXPERIMENTAL TABLE 7

Extraction Performance of Bicyclic Nucleators in Polypropylene Homopolymer

| Additives | Additive Conc. (ppm) | Peak Absorbance, 220–240 nm | Peak Absorbance, 241–350 nm |
|---|---|---|---|
| Control (no nucleator) | — | 0.019 | 0.006 |
| Example A | 2500 | 0.012 | 0.004 |
| 4-MDBS | 2200 | 0.336 | 0.183 |

The data demonstrate that the inventive product in Example 1 shows extraction levels comparable to thermoplastic samples containing no nucleator at all and thus indicates that such thermoplastic may be useful for various end-uses.

Nucleation Density

One method of evaluating the nucleating efficiency of a nucleating agent in a given resin is to calculate the density of nucleating sites per unit volume of polymer as well as comparing such density measurements at differing isothermal crystallization temperatures. The greater the density of nucleating sites, the better the nucleating agent. The higher the ratio of densities between different isotherms, the more versatile the nucleating agent.

For these purposes, the effective nucleation densities for the inventive and comparative nucleating agents were calculated by combining isothermal crystallization kinetic data measured using differential scanning calorimetry and spherulitic growth rate data measured with optical microscopy. A Perkin Elmer DSC-7 was calibrated with an indium metal standard at a heating rate of 20C/min. Polymer samples with a thickness of 250+/−50 microns and a weight of 5.0+/−0.5 mg were encased in aluminum pans. The pans were then heated from 60° C. to 220° C. at 20° C./min, held 2 minutes, rapidly cooled to the isothermal crystallization temperature, and then held at the isothermal crystallization temperature until the crystallization was complete.

The relative crystallinity, C, as a function of time, t, was calculated as demonstrated in [1]. Crystallization Kinetic data were modeled using the Avrami Equation: $1-C=\exp(-Kt^n)$, where K and n are constants. The Avrami equation was rewritten in logarithmic form: $\ln(-\ln(1-C))=\ln K + n \ln t$ and then linear regression was used to find the best values of K and n for relative crystallinities between 0.05 and 0.5. The linear spherulitic growth rate of polypropylene at a given temperature, G, was calculated using the equation $G=1.62 \times 10^{10} \exp(-0.20\ T)$, where T has units of degrees Celsius and G has units of μm/sec [1]. For example, $G(140° C.)=0.0112$ μm/sec.

[1] Journal of Polymer Science: Part B: Polymer Physics, 31, 1395 (1993)

The effective nucleation density, N, was calculated according to $N=3K'/4\pi G^3$, where K' is an Avrami rate constant for the case of three-dimensional growth at a linear growth rate. K' was calculated from K using the following relation: $K'=\ln 2/(\ln 2/K)^{3/n}$ [2]. For example, at an isothermal crystallization temperature of 140° C., homopolymer polypropylene nucleated with 0.1% NA-11UF had Avrami rate constants n=3.21 and K=0.0484 min$^{-3.21}$. The corresponding value of K' was 0.0576 min$^{-3}$=2.67×10$^{-7}$ sec$^{-3}$.

[2] Journal of Applied Polymer Science, 57, 187 (1995)

The following Table shows the nucleation density measurements for various nucleating agents at 140 and 148° C. isotherms. An asterisk for NA-21 indicates that the nucleation density was too low to be measured.

EXPERIMENTAL TABLE 8

Nucleation Density Measurements

| Nucleating Agent | Isothermal T$_c$ (° C.) | Nucleation Density (nuc/cm$^3$) |
|---|---|---|
| 1000 ppm Ex. A[g] | 140 | 6 E 11 |
| 1000 ppm NA-11[h] | 140 | 4 E 10 |
| 2200 ppm NA-21[g] | 140 | 4 E 9 |
| 2500 ppm Camphanic Acid[i] | 140 | 3 E 11 |
| 1000 ppm Ex. A[g] | 148 | 1 E 11 |
| 1000 ppm NA-11[h] | 148 | 2 E 9 |
| 2200 ppm Na-21[g] | 148 | * |
| 2500 ppm Camphanic Acid[i] | 148 | 1 E 10 |

[g]Including 800 ppm of calcium stearate
[h]Including 400 ppm of DHT-4A
[i]Including 800 ppm of lithium stearate Thus, the inventive nucleating agent provided an increase in nucleation density within the test homopolymer polypropylene at least an order of magnitude greater than the closest typical polyolefin nucleating agents. Therefore, such an inventive nucleating agent is defined as one which, at an isothermal T$_c$ of about 148° C. of at least 7E9 (7×10$^9$) nuc/cm$^2$; preferably at least 1E10; still more preferably, at least 5E10; and most preferably at least 1E11, within the test homopolymer polypropylene formulation as noted above, and which, as noted above, does not exhibit any appreciable fugitivity from the thermoplastic formulation during compounding thereof.

Furthermore, it is desirable to measure the effectiveness of a given nucleating agent over a broad range of temperatures. An excellent manner of quantifying such effectiveness measurements over such broad temperature ranges is to calculate a what we have termed a nucleation effectiveness factor. Such a factor (hereinafter referred to as NEF) is, for a given additive, defined as the ratio of the nucleation density provided by a nucleation agent at 148° to the nucleation density provided by the same nucleation agent at 140° C. [in other words NEF=N(148° C.)/N(140° C.)]. A nucleating agent which exhibits a higher nucleation effectiveness factor supplies a large number of heterogeneous nuclei to the polymer over a broad temperature range, which leads to faster polymer crystallization over such a expanded range of temperatures. As noted below in the accompanying Table, and using the results in Experimental Table 8, above, such NEF measurements are as follows:

EXPERIMENTAL TABLE 9

NEF Measurements as Delineated from EXPERIMENTAL TABLE 8

| Nucleating Agent | NEF |
| --- | --- |
| Example A | 0.16 |
| NA-11 | 0.05 |
| Camphanic Acid | 0.03 |

Thus, the inventive nucleating agent is more effective and versatile than the comparative compounds over a broad temperature range. Preferably, such a NEF is thus greater than about 0.06; more preferably, greater than about 0.08; still more preferably greater than about 0.10; and most preferably greater than about 0.12, since the greater the number, the greater the versatility of the nucleating agent.

Having described the invention in detail it is obvious that one skilled in the art will be able to make variations and modifications thereto without departing from the scope of the present invention. Accordingly, the scope of the present invention should be determined only by the claims appended hereto.

That which is claimed is:

1. A polymer additive composition comprising a nucleating agent which conforms with the structure of Formula (I)

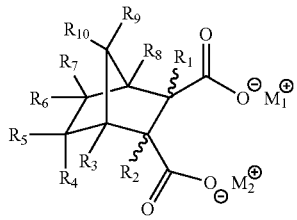

(I)

wherein $M_1$ and $M_2$ are the same or different, or $M_1$ and $M_2$ are combined to form a single moiety, and are independently selected from the group consisting of metal or organic cations, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxyl, $C_1$–$C_8$ alkoxy, $C_1$–$C_9$ alkyleneoxy, amine, and $C_1$–$C_9$ alkylamine, halogen, phenyl, alkylphenyl, and geminal or vicinal carbocyclic having up to 9 carbon atoms;

wherein said nucleating agent induces a peak crystallization temperature of at least 125° C. for a test homopolymer polypropylene formulation comprising said nucleating agent, wherein the unnucleated test homopolymer polypropylene exhibits a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93° C., and wherein said formulation comprising said nucleating agent is extruded then molded into plaques having dimensions of about 51 mm×76 mm×1.27 mm, wherein said peak crystallization temperature is measured by differential scanning calorimetry in accordance with a modified ASTM Test Method D3417-99 at heating and cooling rates of 20° C./minute, and wherein said nucleating agent also exhibits no appreciable fugitivity from said test homopolymer polypropylene formulation during compounding of said test homopolymer polypropylene formulation comprising said nucleating agent, wherein said additive composition is present in a form selected from the group consisting of a powder, a pellet, and a liquid, and wherein said composition also comprises at least one acid scavenger and optionally comprises at least one thermoplastic polymer and at least one compound selected from the group consisting of plasticizers, antioxidants, antimicrobials, flame retardants, light stabilizers, antistatic agents, blowing agents, colored pigments, and any combination thereof.

2. A polymer additive composition comprising a nucleating agent which conforms with the structure of Formula (I)

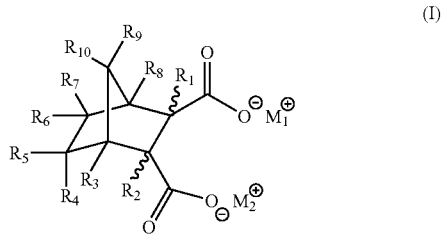

(I)

wherein $M_1$ and $M_2$ are the same or different, or $M_1$ and $M_2$ are combined to form a single moiety, and are independently selected from the group consisting of metal or organic cations, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxyl, $C_1$–$C_9$ alkoxy, $C_1$–$C_9$ alkyleneoxy, amine, and $C_1$–$C_9$ alkylamine, halogen, phenyl, alkylphenyl, and geminal or vicinal carbocyclic having up to 9 carbon atoms;

wherein said nucleating agent induces a crystallization cycle time ($t_{1/2}$) of at most 2.0 minutes in a test homopolymer polypropylene formulation comprising said nucleating agent, wherein the unnucleated test homopolymer polypropylene exhibits a density of about 0.9 g/cc, a melt flow of about 12 g/10 min, a Rockwell Hardness (R scale) of about 90, a tensile strength of about 4,931 psi, an elongation, at yield of about 10%, a flexural modulus of about 203 ksi, an Izod impact strength of about 0.67 ft-lb/in, and a deflection temperature at 0.46 mPa of about 93° C., and wherein said formulation comprising said nucleating agent is extruded then molded into plaques having dimensions of about 61 mm×76 mm×1.27 mm, wherein said $t_{1/2}$ cycle time is measured by differential scanning calorimetry at a constant crystallization temperature of about 140° C., and wherein said nucleator also exhibits no appreciable fugitivity from said polypropylene formulation during compounding of said test homopolymer polypropylene formulation comprising said nucleating agent, wherein said additive composition is present in a form selected from the group consisting of a powder, a pellet, and a liquid, and wherein said composition also comprises at least one acid scavenger and optionally comprises at least one thermoplastic polymer and at least one compound selected from the group consisting of plasticizers, antioxidants, antimicrobials, flame retardants, light stabilizers, antistatic agents, blowing agents, colored pigments, and any combination thereof.

3. A polymer additive composition comprising a nucleating agent which conforms with the structure of Formula (I)

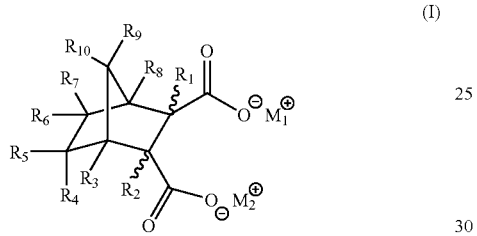

(I)

wherein $M_1$ and $M_2$ are the same or different, or $M_1$ and $M_2$ are combined to form a single moiety, and are independently selected from the group consisting of metal or organic cations, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxyl, $C_1$–$C_9$ alkoxy, $C_1$–$C_9$ alkyleneoxy, amine, and $C_1$–$C_9$ alkylamine, halogen, phenyl, alkylphenyl, and geminal or vicinal carbocyclic having up to 9 carbon atoms;

wherein said nucleating agent induces a standard peak crystallization temperature of at least 123.5° C. in a test homopolymer polypropylene formulation comprising said nucleating agent, wherein the unnucleated test homopolymer polypropylene exhibits a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93° C., and wherein said formulation comprising said nucleating agent is extruded then molded into plaques having dimensions of about 51 mm×76 mm×1.27 mm, wherein said peak crystallization temperature measured by differential scanning calorimetry in accordance with a modified ASTM Test Method D3417-99 at heating and cooling rates of 20° C./minute, wherein said nucleator is present in at most 1500 ppm, wherein said nucleator agent exhibits no appreciable fugitivity from said polypropylene formulation during compounding of said polypropylene formulation with said nucleating agent, and wherein said nucleating agent further induces said peak crystallization temperature within said polypropylene formulation when no calcium stearate is present therein, and wherein said nucleating agent provides a comparative peak crystallization temperature of at most 2° C. lower than said standard peak crystallization for the same polypropylene formulation when at least 800 ppm of calcium stearate is present therein, wherein said additive composition is present in a form selected from the group consisting of a powder, a pellet, and a liquid, and wherein said composition also comprises at least one acid scavenger and optionally comprises at least one thermoplastic polymer and at least one compound selected from the group consisting of plasticizers, antioxidants, antimicrobials, flame retardants, light stabilizers, antistatic agents, blowing agents, colored pigments, and any combination thereof.

4. A polymer additive composition comprising a nucleating agent which conforms with the structure of Formula (I)

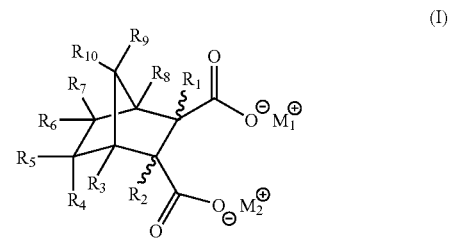

(I)

wherein $M_1$ and $M_2$ are the same or different, or $M_1$ and $M_2$ are combined to form a single moiety, and are independently selected from the group consisting of metal or organic cations, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxyl, $C_1$–$C_9$ alkoxy, $C_1$–$C_9$ alkyleneoxy, amine, and $C_1$–$C_9$ alkylamine, halogen, phenyl, alkylphenyl, and geminal or vicinal carbocyclic having up to 9 carbon atoms;

wherein said nucleating agent produces an effective nucleation density of greater than $7 \times 10^9$ nuclei/cm$^3$ at an isothermal crystallization temperature of about 148° C. in a test homopolymer polypropylene formulation comprising said nucleating agent, wherein the unnucleated test homopolymer polypropylene exhibits a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93° C., and wherein said formulation is extruded then molded into plaques having dimensions of about 51 mm×76 mm×1.27 mm, and wherein said nucleating agent also exhibits no appreciable fugitivity from said test homopolymer polypropylene formulation during compounding of said test homopolymer polypropylene formulation comprising said nucleating agent, wherein said additive composition is present in a form selected from the group consisting of a powder, a pellet, and a liquid, and wherein said composition also comprises at least one acid scavenger and optionally comprises at least one thermoplastic polymer and at least one compound selected from the group consisting of plasticizers, antioxidants, antimicrobials, flame retardants, light stabilizers, antistatic agents, blowing agents, colored pigments, and any combination thereof.

5. A polymer additive composition comprising a nucleating agent which conforms with the structure of Formula (I)

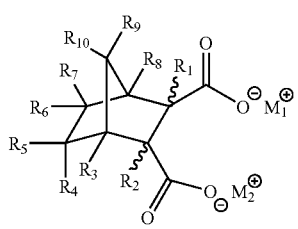

(I)

wherein $M_1$ and $M_2$ are the same or different, or $M_1$ and $M_2$ are combined to form a single moiety, and are independently selected from the group consisting of metal or organic cations, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxyl, $C_1$–$C_9$ alkoxy, $C_1$–$C_9$ alkyleneoxy, amine, and $C_1$–$C_9$ alkylamine, halogen, phenyl, alkylphenyl, and geminal or vicinal carbocyclic having up to 9 carbon atoms;

wherein said nucleating agent exhibits a nucleation effectiveness factor (NEF) of greater than 0.06 in a test homopolymer polypropylene formulation having a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93° C., wherein said formulation is extruded and then molded into plaques having dimensions of about 51 mm×76 mm×1.27 mm, wherein said additive composition is present in a form selected from the group consisting of a powder, a pellet, and a liquid, and wherein said composition also comprises at least one acid scavenger and optionally comprises at least one thermoplastic polymer and at least one compound selected from the group consisting of plasticizers, antioxidants, antimicrobials, flame retardants, light stabilizers, antistatic agents, blowing agents, colored pigments, and any combination thereof.

6. A polymer additive composition comprising a nucleating agent which conforms with the structure of Formula (I)

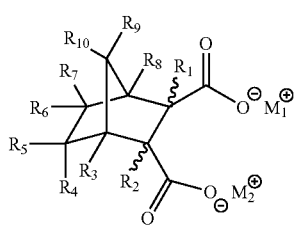

(I)

wherein $M_1$ and $M_2$ are the same or different, or $M_1$ and $M_2$ are combined to form a single moiety, and are independently selected from the group consisting of metal or organic cations, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxyl, $C_1$–$C_9$ alkoxy, $C_1$–$C_9$ alkyleneoxy, amine, and $C_1$–$C_9$ alkylamine, halogen, phenyl, alkylphenyl, and geminal or vicinal carbocyclic having up to 9 carbon atoms;

wherein said nucleating agent induces a peak crystallization temperature of at least 125° C. for a test homopolymer polypropylene formulation comprising said nucleating agent, wherein the unnucleated test homopolymer polypropylene exhibits a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93° C., and wherein said formulation comprising said nucleating agent is extruded then molded into plaques having dimensions of about 51 mm×76 mm×1.27 mm, wherein said peak crystallization temperature is measured by differential scanning calorimetry in accordance with a modified ASTM Test Method D3417-99 at heating and cooling rates of 20° C./minute, and wherein said nucleating agent also exhibits no appreciable fugitivity from said test homopolymer polypropylene formulation during compounding of said test homopolymer polypropylene formulation comprising said nucleating agent, wherein said additive composition is present in a form selected from the group consisting of a powder, a pellet, and a liquid, and wherein said composition also comprises at least one thermoplastic polymer and optionally at least one compound selected from the group consisting of plasticizers, antioxidants, acid scavengers, antimicrobials, flame retardants, light stabilizers, antistatic agents, blowing agents, colored pigments, and any combination thereof.

7. A polymer additive composition comprising a nucleating agent which conforms with the structure of Formula (I)

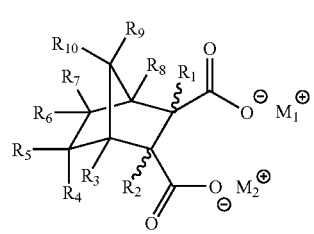

(I)

wherein $M_1$ and $M_2$ are the same or different, or $M_1$ and $M_2$ are combined to form a single moiety, and are independently selected from the group consisting of metal or organic cations, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxyl, $C_1$–$C_9$ alkoxy, $C_1$–$C_9$ alkyleneoxy, amine, and $C_1$–$C_9$ alkylamine, halogen, phenyl, alkylphenyl, and geminal or vicinal carbocyclic having up to 9 carbon atoms;

wherein said nucleating agent induces a crystallization cycle time ($t_{1/2}$) of at most 2.0 minutes in a test homopolymer polypropylene formulation comprising said nucleating agent, wherein the unnucleated test homopolymer polypropylene exhibits a density of about 0.9 g/cc, a melt flow of about 12 g/10 min. a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93° C., and wherein said formulation comprising said nucleating agent is extruded then molded into plaques having dimensions of about 51 mm×76 mm×1.27 mm, wherein said $t_{1/2}$ cycle time is measured by differential scanning calorimetry at a constant crystallization temperature of about 140° C., and wherein said nucleator also exhibits no appreciable fugitivity from said polypropylene formulation during compounding of said test homopolymer polypropylene formulation comprising said nucleating agent, wherein said additive composition is present in a form selected from the group consisting of a powder, a pellet, and a liquid, and wherein said composition also comprises at least one thermoplastic polymer and optionally at least one compound selected from the group consisting of plasticizers, antioxidants, acid scavengers, antimicrobials, flame retardants, light stabilizers, antistatic agents, blowing agents, colored pigments, and any combination thereof.

8. A polymer additive composition comprising a nucleating agent which conforms with the structure of Formula (I)

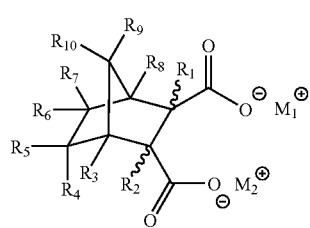

(I)

wherein $M_1$ and $M_2$ are the same or different, or $M_1$ and $M_2$ are combined to form a single moiety, and are independently selected from the group consisting of metal or organic cations, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxyl, $C_1$–$C_9$ alkoxy, $C_1$–$C_9$ alkyleneoxy, amine, and $C_1$–$C_9$ alkylamine, halogen, phenyl, alkylphenyl, and geminal or vicinal carbocyclic having up to 9 carbon atoms;

wherein said nucleating agent induces a standard peak crystallization temperature of at least 123.5° C. in a test homopolymer polypropylene formulation comprising said nucleating agent, wherein the unnucleated test homopolymer polypropylene exhibits a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93° C., and wherein said formulation comprising said nucleating agent is extruded then molded into plaques having dimensions of about 51 mm×76mm×1.27 mm, wherein said peak crystallization temperature measured by differential scanning calorimetry in accordance with a modified ASTM Test Method D3417-99 at heating and cooling rates of 20° C./minute, wherein said nucleator is present in at most 1500 ppm, wherein said nucleator agent exhibits no appreciable fugitivity from said polypropylene formulation during compounding of said polypropylene formulation with said nucleating agent, and wherein said nucleating agent further induces said peak crystallization temperature within said polypropylene formulation when no calcium stearate is present therein, and wherein said nucleating agent provides a comparative peak crystallization temperature of at most 2° C. lower than said standard peak crystallization for the same polypropylene formulation when at least 800 ppm of calcium stearate is present therein, wherein said additive composition is present in a form selected from the group consisting of a powder, a pellet, and a liquid, and wherein said composition also comprises at least one thermoplastic polymer and optionally at least one compound selected from the group consisting of plasticizers, antioxidants, acid scavengers, antimicrobials, flame retardants, light stabilizers, antistatic agents, blowing agents, colored pigments, and any combination thereof.

9. A polymer additive composition comprising a nucleating agent which conforms with the structure of Formula (I)

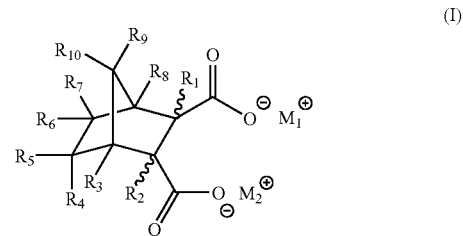

(I)

wherein $M_1$ and $M_2$ are the same or different, or $M_1$ and $M_2$ are combined to form a single moiety, and are independently selected from the group consisting of metal or organic cations, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxyl, $C_1$–$C_9$ alkoxy, $C_1$–$C_9$ alkyleneoxy, amine, and $C_1$–$C_9$ alkylamine, halogen, phenyl, alkylphenyl, and geminal or vicinal carbocyclic having up to 9 carbon atoms;

wherein said nucleating agent produces an effective nucleation density of greater than $7\times10^9$ nuclei/cm$^3$ at an isothermal crystallization temperature of about 148° C. in a test homopolymer polypropylene formulation comprising said nucleating agent, wherein the unnucleated test homopolymer polypropylene exhibits a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93° C. and wherein said formulation is extruded then molded into plaques having dimensions of about 51 mm×76 mm×1.27 mm, and wherein said nucleating agent also exhibits no appreciable fugitivity from said test homopolymer polypropylene formulation during compounding of said test homopolymer polypropylene formulation comprising said nucleating agent, wherein said additive composition is present in a form selected from the group consisting of a powder, a pellet, and a liquid, and wherein said composition also comprises at least one thermoplastic polymer and optionally at least one compound selected from the group consisting of plasticizers, antioxidants, acid scavengers, antimicrobials, flame retarda, light stabilizers, antistatic agents, blowing agents, colored pigments, and any combination thereof.

10. A polymer additive composition comprising a nucleating agent which conforms with the structure of Formula (I)

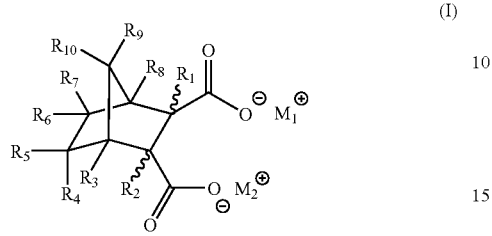

(I)

wherein $M_1$ and $M_2$ are the same or different, or $M_1$ and $M_2$ are combined to form a single moiety, and are independently selected from the group consisting of metal or organic cations, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxyl, $C_1$–$C_9$ alkoxy, $C_1$–$C_9$ alkyleneoxy, amine, and $C_1$–$C_9$ alkylamine, halogen, phenyl, alkylphenyl, and geminal or vicinal carbocyclic having up to 9 carbon atoms;

wherein said nucleating agent exhibits a nucleation effectiveness factor (NEF) of greater than 0.06 in a test homopolymer polypropylene formulation having a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature of at 0.46 mPa of about 93° C., wherein said formulation is extruded and then molded into plaques having dimensions of about 51 mm×76 mm×1.27 mm, wherein said additive composition is present in a form selected from the group consisting of a powder, a pellet, and a liquid, and wherein said composition also comprises at least one thermoplastic polymer and optionally at least one compound selected from the group consisting of plasticizers, antioxidants, acid scavenger, antimicrobials, flame retardants, light stabilizers, antistatic agents, blowing agents, colored pigments, and any combination thereof.

* * * * *

UNITED STATES PATENT AND TRADEMARK OFFICE
CERTIFICATE OF CORRECTION

PATENT NO. : 7,094,820 B2
APPLICATION NO. : 10/288040
DATED : August 22, 2006
INVENTOR(S) : Xiaodong Edward Zhao and Darin L. Dotson It is certified that error appears in the above-identified patent and that said Letters Patent is hereby corrected as shown below:

Column 26, Claim 10, line 12 "of at 0.46" should read "at 0.46"

Signed and Sealed this

Twenty-first Day of November, 2006

JON W. DUDAS
*Director of the United States Patent and Trademark Office*